US010603496B2

United States Patent
Ternes et al.

(10) Patent No.: US 10,603,496 B2
(45) Date of Patent: Mar. 31, 2020

(54) CONDUCTION PATHWAY DRIVEN MULTI-SITE PACING MANAGEMENT

(71) Applicant: Cardiac Pacemakers, Inc., St. Paul, MN (US)

(72) Inventors: David J. Ternes, Roseville, MN (US); Keith L. Herrmann, Minneapolis, MN (US); Britta Catherine Veldman, White Bear Township, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 142 days.

(21) Appl. No.: 15/794,266

(22) Filed: Oct. 26, 2017

(65) Prior Publication Data
US 2018/0126173 A1 May 10, 2018

Related U.S. Application Data

(60) Provisional application No. 62/419,627, filed on Nov. 9, 2016.

(51) Int. Cl.
*A61N 1/368* (2006.01)
*A61N 1/05* (2006.01)
(Continued)

(52) U.S. Cl.
CPC ......... *A61N 1/36843* (2017.08); *A61N 1/056* (2013.01); *A61N 1/3682* (2013.01);
(Continued)

(58) Field of Classification Search
CPC .......................... A61N 1/3684; A61N 1/36842
See application file for complete search history.

(56) References Cited

U.S. PATENT DOCUMENTS

| 5,893,882 A | 4/1999 | Peterson et al. |
|---|---|---|
| 6,650,135 B1 | 11/2003 | Mautz et al. |

(Continued)

FOREIGN PATENT DOCUMENTS

| CN | 109952127 A | 6/2019 |
|---|---|---|
| WO | WO-2018089201 A1 | 5/2018 |

OTHER PUBLICATIONS

Di Pede, Francesco, et al., "Hemodynamic Effects of Atrial Septal Pacing in Cardiac Resynchronization Therapy Patients", Journal of Cardiovascular Electrophysiology vol. 16, No. 12, Dec. 2005, pp. 1273-1278.

(Continued)

*Primary Examiner* — Kennedy Schaetzle
(74) *Attorney, Agent, or Firm* — Schwegman Lundberg & Woessner, P.A.

(57) ABSTRACT

An apparatus comprises a stimulus circuit, a cardiac signal sensing circuit, and a control circuit. The cardiac signal sensing circuit senses a cardiac activity signal using a sensing channel. The stimulus circuit provides electrical pulse energy to a first pacing channel that includes a first left ventricular (LV) electrode and a second pacing channel that includes a second LV electrode. The control circuit initiates delivery of electrical pulse energy using the first and second pacing channels according to a first multi-site LV pacing mode; determines a cardiac event associated with a change in cardiac conduction path using a sensed cardiac activity signal; and changes to a second LV pacing mode in response to determining the cardiac event. The second LV pacing mode is different from the first multi-site LV pacing mode in one or more of a pacing site location and inter-electrode stimulus timing.

20 Claims, 6 Drawing Sheets

(51) Int. Cl.
*A61N 1/37* (2006.01)
*A61N 1/365* (2006.01)
*A61N 1/39* (2006.01)

(52) U.S. Cl.
CPC ......... *A61N 1/3684* (2013.01); *A61N 1/3686* (2013.01); *A61N 1/3688* (2013.01); *A61N 1/36507* (2013.01); *A61N 1/36514* (2013.01); *A61N 1/36842* (2017.08); *A61N 1/3702* (2013.01); *A61N 1/39622* (2017.08)

(56) References Cited

U.S. PATENT DOCUMENTS

| | | | |
|---|---|---|---|
| 7,272,438 | B2 | 9/2007 | Kroll et al. |
| 7,292,887 | B2 | 11/2007 | Salo et al. |
| 8,332,033 | B2 | 12/2012 | Reed et al. |
| 8,447,400 | B2 | 5/2013 | More et al. |
| 8,560,067 | B2 | 10/2013 | Salo et al. |
| 8,588,909 | B1 | 11/2013 | Levine |
| 8,718,767 | B2 | 5/2014 | Lindgren |
| 8,897,874 | B2 | 11/2014 | Stahmann et al. |
| 2002/0177879 | A1* | 11/2002 | Ding ............... A61N 1/368 607/9 |
| 2003/0009197 | A1* | 1/2003 | Helland ............ A61N 1/368 607/9 |
| 2003/0078627 | A1 | 4/2003 | Casavant et al. |
| 2007/0078489 | A1* | 4/2007 | Meyer ............... A61N 1/371 607/9 |
| 2007/0106334 | A1 | 5/2007 | Ziegler et al. |
| 2007/0191892 | A1 | 8/2007 | Mullen et al. |
| 2008/0177344 | A1* | 7/2008 | Maskara ............ A61N 1/3627 607/25 |
| 2013/0131750 | A1* | 5/2013 | Stadler ............. A61N 1/3627 607/25 |
| 2016/0129263 | A1 | 5/2016 | Demmer et al. |
| 2016/0228708 | A1 | 8/2016 | Ternes et al. |
| 2016/0228709 | A1 | 8/2016 | Ternes et al. |
| 2016/0228710 | A1* | 8/2016 | Thakur ............. A61N 1/3686 |

OTHER PUBLICATIONS

Kirk, Jonathan A., et al., "Pacemaker-Induced Transient Asynchrony Suppresses Heart Failure Progression", Sci Transl Med. 7(319), (Dec. 2015), 1-25.
Liang, Hsin-Yuch, et al., "Influence of Atrial Function and Mechanical Synchrony on LV Hemodynamic Status in Heart Failure Patients on Resynchronization Therapy", JACC, vol. 4, No. 7, 2011, (2011), 691-698.
Spragg, David, et al., "Regional Alterations in Protein Expression in the Dyssynchronous Failing Heart", Circulation; 108, (2003), 929-932.
Vanderheyden, Marc, et al., "Cellular Electrophysiological Abnormalities in Dyssynchronous Hearts and During CRT", J. of Cardiovasc. Trans. Res. (2011) pp. 1-8.
"International Application Serial No. PCT/US2017/058425, International Preliminary Report on Patentability dated May 23, 2019", 9 pgs.
"International Application Serial No. PCT/US2017/058425, International Search Report dated Jan. 22, 2018", 6 pgs.
"International Application Serial No. PCT/US2017/058425, Written Opinion dated Jan. 22, 2018", 7 pgs.

* cited by examiner

FIG. 8

CONDUCTION PATHWAY DRIVEN MULTI-SITE PACING MANAGEMENT

CLAIM OF PRIORITY

This application claims the benefit of priority under 35 U.S.C. § 119(e) of U.S. Provisional Patent Application Ser. No. 62/419,627, filed on Nov. 9, 2016, which is herein incorporated by reference in its entirety.

BACKGROUND

Ambulatory medical devices can be used to treat patients or subjects using electrical or other therapy, or to aid a physician or caregiver in patient diagnosis through internal monitoring of a patient's condition. Some types of ambulatory medical devices may be implantable or partially implantable. Some examples include cardiac function management (CFM) devices such as implantable pacemakers, implantable cardioverter defibrillators (ICDs), cardiac resynchronization therapy devices (CRTs), and devices that include a combination of such capabilities. The devices may include one or more electrodes in communication with one or more sense amplifiers to monitor electrical heart activity within a patient, and often include one or more sensors to monitor one or more other internal patient parameters. The devices may be implanted subcutaneously and may include electrodes that are able to sense cardiac signals without being in direct contact with the patient's heart. Other examples of implantable medical devices (IMDs) include implantable diagnostic devices, implantable drug delivery systems, or implantable devices with neural stimulation capability (e.g., vagus nerve stimulator, baroreflex stimulator, carotid sinus stimulator, deep brain stimulator, sacral nerve stimulator, etc.).

Operation of an ambulatory medical device is typically optimized for particular patient by a caregiver, such as by programming different device operating parameters or settings for example. Manufacturers of such devices continue to improve and add functionality to the devices, which can make them complicated to optimize for a particular patient. The inventors have recognized a need for improved optimization of device-based therapy.

OVERVIEW

The present subject matter relates to providing multi-site electrical stimulation therapy. An example multi-site electrical stimulation therapy is multi-site pacing stimulation delivered to multiple sites within the same chamber of the heart such as the left ventricle.

An apparatus example of the present subject matter is for electrical coupling to a plurality of implantable electrodes. The apparatus example includes a stimulus circuit, a cardiac signal sensing circuit, and a control circuit. The cardiac signal sensing circuit senses a cardiac activity signal using a sensing channel. The stimulus circuit provides electrical pulse energy to a first pacing channel that includes a first left ventricular (LV) electrode and a second pacing channel that includes a second LV electrode. The control circuit initiates delivery of electrical pulse energy using the first and second pacing channels according to a first multi-site LV pacing mode; determines a cardiac event associated with a change in cardiac conduction path using a sensed cardiac activity signal; and changes to a second LV pacing mode in response to determining the cardiac event. The second LV pacing mode is different from the first multi-site LV pacing mode in one or more of a pacing site location and an inter-electrode stimulus timing.

Multi-site pacing of a heart chamber may add complexity to the programming of parameter values for electrical stimulation therapy. The patient prescribed a device that provides multi-site pacing therapy may benefit from optimizing the therapy for changing patient conditions.

This section is intended to provide a brief overview of subject matter of the present patent application. It is not intended to provide an exclusive or exhaustive explanation of the invention. The detailed description is included to provide further information about the present patent application such as a discussion of the dependent claims and the interrelation of the dependent and independent claims in addition to the statements made in this section.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, the various examples discussed in the present document.

DETAILED DESCRIPTION

An ambulatory medical device can include one or more of the features, structures, methods, or combinations thereof described herein. For example, a cardiac function management device may be implemented to include one or more of the advantageous features or processes described below. It is intended that such a cardiac function management device, or other implantable or partially implantable device, need not include all of the features described herein, but may be implemented to include selected features that provide for unique structures or functionality. Such a device may be implemented to provide a variety of therapeutic or diagnostic functions.

Figure 1:
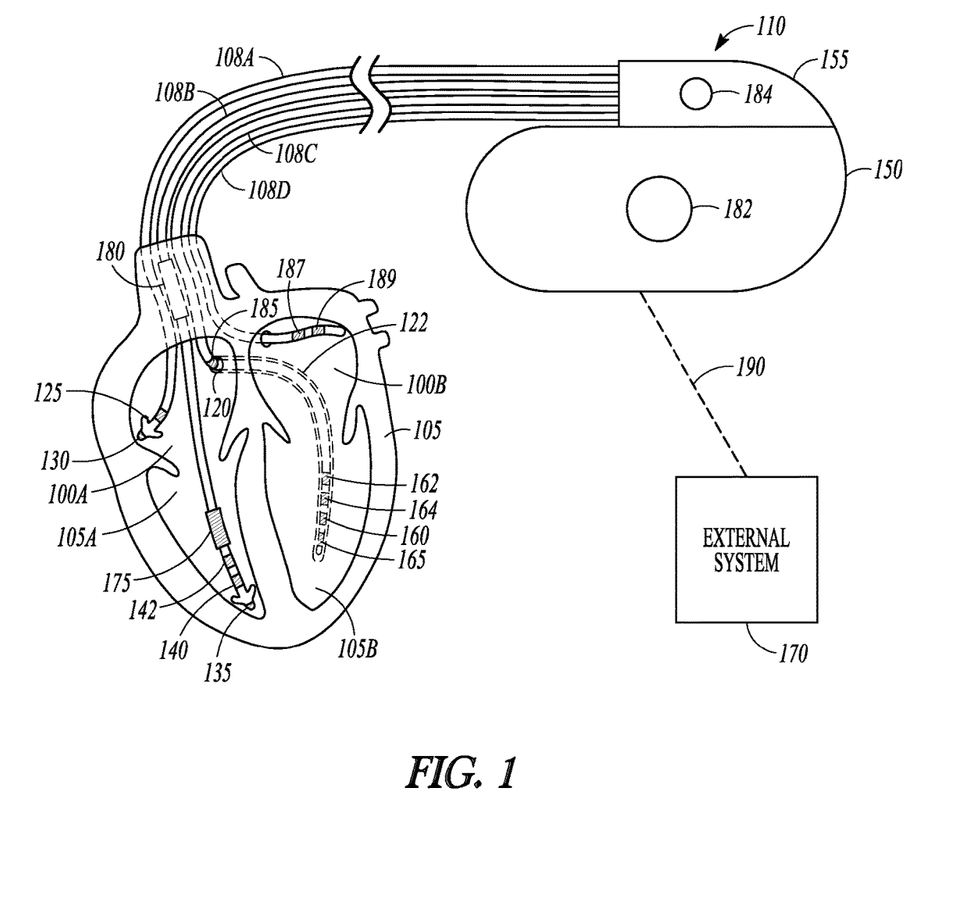
FIG. 1 is an illustration of an example of portions of a system that includes an implantable medical device.

FIG. 1 is an illustration of portions of a system that includes an ambulatory medical device that is an IMD 110. Examples of IMD 110 include, without limitation, a pacemaker, a defibrillator, a cardiac resynchronization therapy (CRT) device, or a combination of such devices. In other examples, the IMD is a neurostimulator such as among other things a vagus nerve stimulator, baroreflex stimulator, carotid sinus stimulator, deep brain stimulator, or sacral nerve stimulator. The system 100 also typically includes an IMD programmer or other external system 170 that communicates wireless signals 190 with the IMD 110, such as by using radio frequency (RF) or other telemetry signals.

The IMD 110 can be coupled by one or more leads 108A-D to heart 105. Cardiac leads 108A-D include a proximal end that is coupled to IMD 110 and a distal end, coupled by electrical contacts or "electrodes" to one or more portions of a heart 105. The electrodes typically deliver cardioversion, defibrillation, pacing, or resynchronization therapy, or combinations thereof to at least one chamber of the heart 105. The electrodes may be electrically coupled to sense amplifiers to sense electrical cardiac signals. Sometimes the sensing circuits and electrodes are referred to as sensing channels. For example, circuitry used to sense signals in an atrium is referred to as an atrial sensing channel, and circuitry used to sense signals in a ventricle is referred to as a ventricular sensing channel. When direction is taken into account due to position of one or more sensing electrodes, the sensing channel can be referred to as a sensing vector.

Sensed electrical cardiac signals can be sampled to create an electrogram. An electrogram can be analyzed by the IMD and/or can be stored in the IMD and later communicated to an external device where the sampled cardiac signals can be displayed for analysis.

Heart 105 includes a right atrium 100A, a left atrium 100B, a right ventricle 105A, a left ventricle 105B, and a coronary sinus 120 extending from right atrium 100A. Right atrial (RA) lead 108A includes electrodes (electrical contacts, such as ring electrode 125 and tip electrode 130) disposed in an atrium 100A of heart 105 for sensing signals, or delivering pacing therapy, or both, to the atrium 100A. Electrodes used to provide pacing therapy can be referred to as pacing channels. When direction is taken into account due to position of one or more pacing electrodes, the pacing channel can be referred to as a pacing vector. Similarly, electrodes used to sense cardiac signals with sense amplifiers can be referred to as sensing channels, and when direction is taken into account a sensing channel can be referred to as a sensing vector.

Right ventricular (RV) lead 108B includes one or more electrodes, such as tip electrode 135 and ring electrode 140, for sensing signals, delivering pacing therapy, or both sensing signals and delivering pacing therapy. RV lead 108B can include one or more additional ring electrodes 142 to provide multi-site pacing to the RV. Lead 108B optionally also includes additional electrodes, such as electrodes 175 and 180, for delivering atrial cardioversion, atrial defibrillation, ventricular cardioversion, ventricular defibrillation, or combinations thereof to heart 105. Such electrodes typically have larger surface areas than pacing electrodes in order to handle the larger energies involved in defibrillation. Lead 108B optionally provides resynchronization therapy to the heart 105. Resynchronization therapy is typically delivered to the ventricles in order to better synchronize the timing of depolarizations between ventricles.

The IMD 110 can include a third cardiac lead 108C attached to the IMD 110 through the header 155. The third cardiac lead 108C includes electrodes 160, 162, 164, and 165 placed in a coronary vein 122 lying epicardially on the left ventricle (LV) 105B via the coronary vein. The number of electrodes shown in the Figure is only an example and other arrangements are possible. For instance, the third cardiac lead 108C may include less electrodes (e.g., one or two electrodes) or more electrodes (e.g., eight or more electrodes) than the example shown, and may include a ring electrode 185 positioned near the coronary sinus (CS) 120. LV lead 108C can provide multi-site pacing to the LV.

In addition to cardiac leads 108A, 108B, 108C, or in the alternative to one or more of cardiac leads 108A, 108B, 108C, the IMD 110 can include a fourth cardiac lead 108D that includes electrodes 187 and 189 placed in a vessel lying epicardially on the left atrium (LA) 100B. The IMD 110 may include multiple LV leads (disposable in different LV veins or the same LV vein) that include and that may each have two or more electrodes.

The IMD 110 can include a hermetically-sealed IMD housing or can 150, and the IMD 110 can include an electrode 182 formed on the IMD can 150. The IMD 110 may include an IMD header 155 for coupling to the cardiac leads, and the IMD header 155 may also include an electrode 184. Cardiac pacing therapy can be delivered in a unipolar mode using the electrode 182 or electrode 184 and one or more electrodes formed on a lead. Cardiac pacing therapy can be delivered in an extended bipolar pacing mode using only one electrode of a lead (e.g., only one electrode of LV lead 108C) and one electrode of a different lead (e.g., only one electrode of RV lead 108B). Cardiac pacing therapy can be delivered in a monopolar pacing mode using only one electrode of a lead without a second electrode.

Lead 108B can include a defibrillation RV coil electrode 175 located proximal to tip and ring electrodes 135, 140, and a second defibrillation coil electrode 180 located proximal to the RV coil electrode 175, tip electrode 135, and ring electrode 140 for placement in the superior vena cava (SVC). In some examples, high-energy shock therapy is delivered from the first or RV coil 175 to the second or SVC coil 180. In some examples, the SVC coil 180 is electrically tied to the electrode 182 formed on the IMD can 150. This improves defibrillation by delivering current from the RV coil electrode 175 more uniformly over the ventricular myocardium. In some examples, the therapy is delivered from the RV coil 175 only to the electrode 182 formed on the IMD can 150. In some examples, the coil electrodes 175, 180 are used in combination with other electrodes for sensing signals.

Note that the specific arrangement of leads and electrodes shown in the illustrated example of FIG. 1 is intended to be non-limiting. An IMD can be configured with a variety of electrode arrangements including transvenous, endocardial, and epicardial electrodes (e.g., an epicardial patch that may include dozens of electrodes), and/or subcutaneous, non-intrathoracic electrodes. An IMD 110 can be connectable to subcutaneous array or lead electrodes (e.g., non-intrathoracic electrodes or additional LV leads implantable along the LV wall, and leads implantable in one or both atria) that can be implanted in other areas of the body to help "steer" electrical currents produced by IMD 110. An IMD can be leadless (e.g., a leadless pacemaker). A leadless IMD may be placed in a heart chamber (e.g., RV or LV) and multiple electrodes of the leadless IMD may contact multiple tissue sites of the heart chamber.

As explained previously herein, a CRM device may be configured to provide multi-site pacing, in which electrical stimulation pulses are provided to multiple sites within the same heart chamber. For example, in the electrode configuration shown in FIG. 1, pacing can be provided to the LV using a first pacing channel that includes can electrode 182 as the pacing channel anode and LV electrode 165 as the pacing channel cathode, and using a second pacing channel that includes the can electrode 182 and LV electrode 164. This may be useful to improve coordination of a contraction of the heart chamber, especially contraction of the left ventricle. The example of FIG. 1 shows that there can be several pacing channels available for multi-site pacing.

However, configuring one combination of electrodes for multi-site pacing for the patient may not be the optimum configuration for every cardiac event experienced by the patient. Different cardiac depolarization events can have different cardiac conduction paths. For instance, an intrinsic atrial depolarization occurs because the sinus node (located at the junction of the high right atrium and the SVC) activates normally and conduction of the depolarization wave front uses native conduction pathways. A normal intrinsic depolarization continues to the atrioventricular (AV) conduction axis and then to the ventricles. A patient receiving bradycardia therapy may be experiencing a problem with conduction along the AV conduction pathway or with conduction in one or both of the ventricles. This may require delivering electrical pulse energy to one or both of the ventricles after a specified AV delay following an atrial sense event (AV sense delay). In some examples, multi-site LV pacing is provided following an atrial sense event to coordinate depolarization of the LV with the RV.

For some bradycardia therapies, if a CRM device does not sense an atrial event before the expiration of a timer, the CRM device delivers an electrical pulse (a pacing pulse) to the atrium to induce cardiac depolarization and contraction in the atrium. The electrical pulse energy is provided using an electrode which may be included in a cardiac lead such as RA lead 108A in FIG. 1. An atrial pace pulse may also be delivered in the presence of noise when the atrial sensing channel cannot track intrinsic atrial events due to noise on the RA lead. For an atrial paced event the depolarization originates at the location of the electrode, which is disposed at a different location than the sinus node. Thus, the depolarization resulting from an electrical pulse starts at a different location than an intrinsic depolarization, and the conduction of the depolarization wave front can use a slower conduction path than the native conduction path. Ventricular pacing then follows an AV pace delay.

Figure 2:
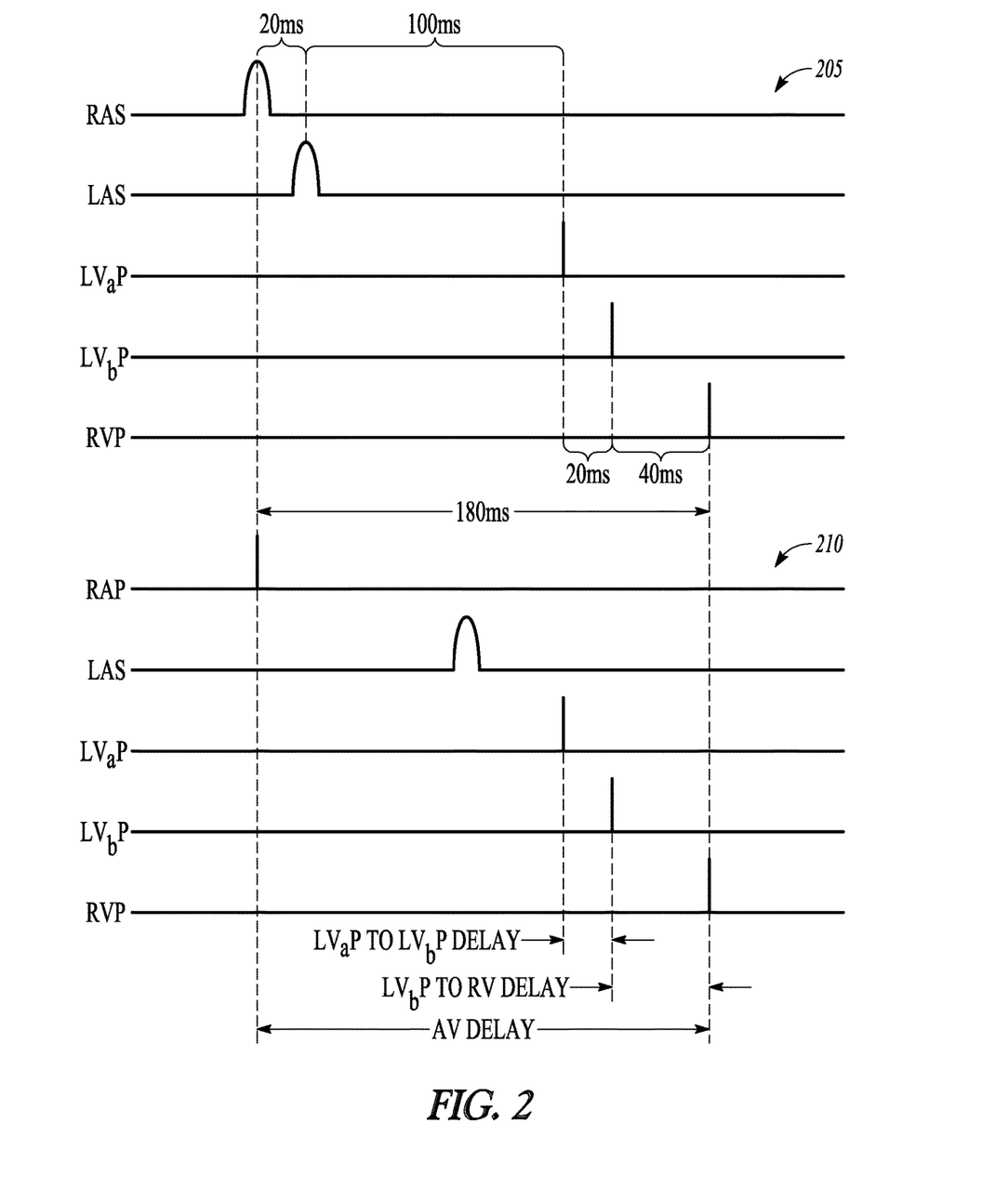
FIG. 2 is a timing diagram of cardiac activation signals.

Using the same timing for ventricular multi-site pacing in response to both an atrial sensed event and an atrial paced event may not be the most optimum setting for the patient. FIG. 2 is a timing diagram of cardiac activation signals. The top graph 205 shows activation signals corresponding to an intrinsic event occurring in the RA (RAS) and an intrinsic event occurring in the LA (LAS). The RV is paced (RVP) in response to the intrinsic atrial event after a sensed AV delay of 180 milliseconds (180 ms). The activation signals LVaP and LVbP represent pacing energy delivered to the LV at electrodes LVa and LVb respectively, which are located at different LV pacing sites. In the example of FIG. 2, an electrical pulse is delivered to electrode LVa 20 ms before an electrical pulse is delivered to electrode LVb. An electrical pulse is delivered to electrode LVb 40 ms before the RV is paced.

The bottom graph 210 shows activation signals corresponding to a paced event occurring in the RA (RAP) and an intrinsic event occurring in the LA (LAS). Because of the change in conduction path associated with RAP, there is a longer delay before the intrinsic event in the LA (LAS). This longer delay may result in pacing the LV (LVaP) too close to the time of the LA ejection or kick (LAS), which may result in less sufficient filling of the LV resulting in reduced cardiac output. This may be especially true if the CRM device provides rate responsive pacing in which the CRM device increases the pacing rate in response to detected patient activity. Increasing the atrial pacing rate may include dynamically shortening the paced AV delay which can cause the LA kick (LAS) to occur too close in time to the pacing of a proximal LV pacing site.

A better approach may be to change the multi-site ventricular stimuli timing to take into account the conduction changes between the paced and sensed events. This can involve changing the inter-electrode timing or changing one or more pacing locations or pacing sites. For example, the LVaP time can be moved later to match the LVbP time and move the LVaP event away from the LAS event to allow more time for ventricular filling. In another example, the time between the LVbP and the RVP can be shortened to move the LVaP event away from the LAS event. In another example, the LVaP is dropped altogether and the device changes to a single-site LV pacing mode. In another example, the LVa pacing site is changed to a site farther away from the LA. It can be seen in the example of FIG. 2 that conduction differences between an intrinsic atrial depolarization and pacing the atrium can change the optimal ventricular pacing for the patient.

In another example, a CRM device may be configured to sense for ventricular events (e.g., in the RV) without regard to events occurring in the atria of the patient. Different multi-site ventricular timing in response to ventricular sensed events and ventricular paced events may also be desirable for the patient receiving this type of therapy. In another example, the patient may be experiencing premature ventricular contraction (PVCs). It may be desirable to use different timing for multi-site ventricular pacing in the presence of PVCs due to the changed ventricular conduction path of the PVCs. In still another example, the patient may experience an episode of non-sustained ventricular tachyarrhythmia. It may be desirable to use different timing for multi-site ventricular pacing when such as episode occurs to account for transient conduction changes in the ventricles as the heart adjusts to the impact of the unstable hemodynamics associated with the ventricular tachyarrhythmia. It may also be desirable to use different timing for multi-site ventricular pacing when the patient experiences a sustained episode of ventricular tachycardia (VT) that was terminated by anti-tachycardia pacing (ATP). In still another example, it may be desirable to use different timing for multi-site ventricular pacing after high electrical energy defibrillation or cardioversion shock therapy is delivered to the patient because changes in conduction pathways resulting from delivery of the shock (e.g., changes due to cardiac tissue being in a stunned state).

Figure 3:
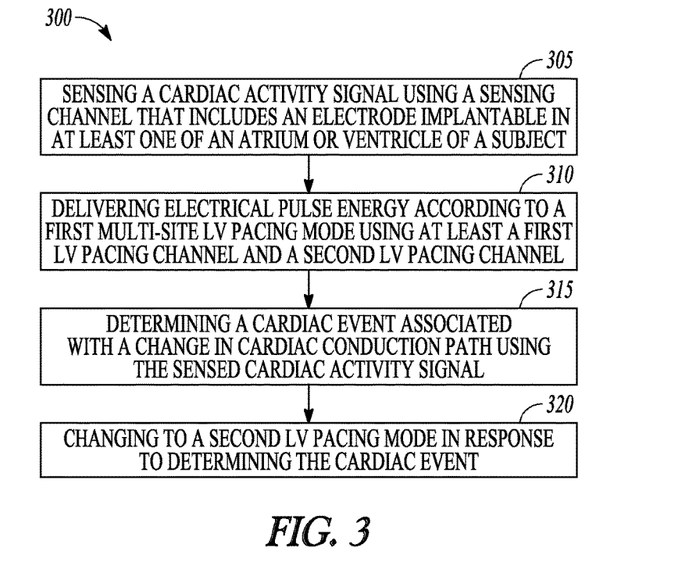
FIG. 3 is a flow diagram of an example of a method of controlling operation of an ambulatory medical device

FIG. 3 is a flow diagram of an example of a method 300 of controlling operation of an ambulatory medical device such as the IMD 110 of FIG. 1. At 305, an electrical cardiac activity signal is sensed using a sensing channel that includes an electrode implantable in at least one of an atrium or ventricle of a subject. At 310, electrical pulse energy is delivered to multiple sites in the LV according to a first multi-site LV pacing mode. The electrical pulse energy is pacing therapy delivered using at least a first LV pacing channel and a second LV pacing channel. An LV pacing channel includes at least one LV electrode. For example, the first LV pacing channel can include LV electrodes 162 and 164 in FIG. 1, and the second LV pacing channel can include LV electrodes 160 and 165. In another example, the first LV pacing channel can include LV electrode 162 and can electrode 182, and the second LV pacing channel can include LV electrode 160 and can electrode 182. In still another example, the multi-site pacing can be delivered to four pacing channels that include one of LV electrodes 162, 164, 160, and 165 and the can electrode 182, or the RV coil electrode 175.

At 315, a cardiac event that is associated with a change in cardiac conduction path is determined or detected by the device using the sensed cardiac activity signal. The cardiac event may be any of a change atrial sensing to atrial pacing, a PVC, an episode in non-sustained ventricular tachyarrhythmia, atrial arrhythmia successfully treated with anti-tachycardia pacing (ATP), or a high energy defibrillation/cardioversion shock delivered to the patient or subject. Other examples include delivering a pace pulse to a vagus nerve stimulation site, or a change in patient drug therapy that can affect cardiac conduction.

At 320, the device changes to a second LV pacing mode in response to determining the cardiac event. The second LV pacing mode is different from the first LV pacing mode to account for changes in conduction paths resulting from the cardiac event. In some examples, the second LV pacing mode is also a multi-site LV pacing mode that may deliver pacing energy to one or more different pacing site locations. In some examples, electrical pulse energy is delivered to only one pacing site in the LV in the second LV pacing mode. The second LV pacing mode also may include delivery of pacing energy using different inter-electrode stimulus timing, or different electrodes.

Figure 4:
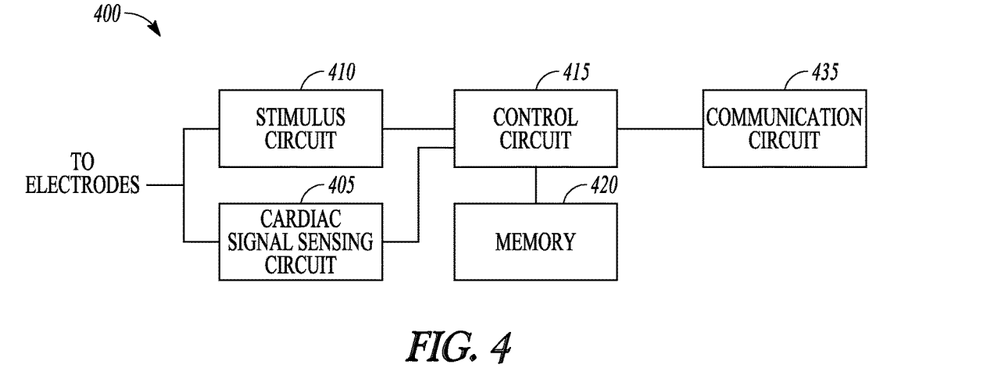
FIG. 4 is a block diagram of portions of an example of an ambulatory medical device that provides multi-site pacing therapy.

FIG. 4 is a block diagram of portions of an example of an ambulatory medical device to provide multi-site LV pacing therapy. The device 400 includes a cardiac signal sensing circuit 405 and a stimulus circuit 410 that can be electrically coupled to implantable electrodes. The cardiac signal sensing circuit 405 senses a cardiac activity signal using a sensing channel that includes an electrode implantable in an atrium or ventricle. The stimulus circuit 410 provides electrical pulse energy using at least a first LV pacing channel that includes a first LV electrode and a second LV pacing channel that includes a second LV electrode. The device may include more than two LV pacing channels. For instance, the device in FIG. 1 includes four LV pacing electrodes, but can be configured with many different pacing channels if one takes into account pacing from any LV electrode to the IMD can 150, pacing from the LV electrodes to an RV electrode, bipolar combinations of the LV electrodes, etc.

The device 400 also includes a control circuit 415 electrically coupled to the cardiac signal sensing circuit 405 and the stimulus circuit 410. The control circuit 415 can include a microprocessor, a digital signal processor, application specific integrated circuit (ASIC), or other type of processor, interpreting or executing instructions included in software or firmware. The control circuit 415 can include sub-circuits to perform the functions described. These sub-circuits may include software, hardware, firmware or any combination thereof. Multiple functions can be performed in one or more of the sub-circuits as desired.

The control circuit 415 initiates delivery of electrical pulse energy using the first and second pacing channels according to a first multi-site LV pacing mode. The control circuit 415 can also determine cardiac events associated with a change in cardiac conduction paths. In response to determining such a cardiac event, the control circuit may change the pacing therapy to include a second LV pacing mode. The parameters for LV pacing in the second LV pacing mode are different from the parameters in the first LV pacing mode. The parameters can include which of the available pacing site locations are used in the pacing therapy, and can include the values of inter-electrode stimulus timing used in the pacing therapy. The parameters may be stored in a memory circuit 420 integral to, or operatively coupled to, the control circuit 415.

In some examples, the device 400 includes an atrial sensing channel and an atrial pacing channel that include at least one atrial electrode. The cardiac event can be a change from a cardiac cycle in which an intrinsic atrial event is sensed to a cardiac cycle in which a pace pulse is scheduled to be delivered because no intrinsic atrial event occurred within a specified time frame from the last cardiac event (paced or sensed). The control circuit 415 may load parameters for the first LV pacing mode when the intrinsic atrial event is detected and load parameters for the second LV pacing mode when delivering a pace pulse to the atrium. In certain examples, the control circuit 415 loads a first of CRT parameters for multi-site pacing in the first LV pacing mode and loads a second set of CRT parameters for multi-site pacing in the second LV pacing mode.

Other examples of the cardiac event include detection of one or more PVCs, detection of an episode of non-sustained ventricular tachyarrhythmia, or a determination that a high energy defibrillation/cardioversion shock delivered to the patient or subject. The control circuit 415 may operate normally in the first LV pacing mode and load parameters for the second LV pacing mode when detecting the PVCs, when detecting the non-sustained ventricular tachyarrhythmia, or when determining that the heart is in a post-shock condition.

As explained previously herein, the control circuit 415 can change the electrode pacing sites used in the second LV pacing from the electrode pacing sites used in the first LV pacing mode. In some examples, the control circuit 415 reduces or increases the number of pacing sites when operating in the second LV pacing mode than when operating in the first multi-site LV pacing mode. In some examples, the control circuit 415 initiates delivery of electrical pulse energy to only one pacing site in the LV when operating in the second LV pacing mode. This may be useful when changing modes from responding to an intrinsic atrial event to responding to an atrial paced event as shown in the example of FIG. 2. Reducing the number of sites can accommodate the slower conduction paths due to the atrial pacing while still allowing sufficient ventricular fulling. In the example of the IMD of FIG. 1, this can include removing or excluding LV electrode 162 (or the most proximal LV electrode of the LV lead 108C) from the delivery of electrical pulse energy to the LV when operating in the second LV pacing mode. This provides more distance and hence longer time between the end of contraction in the LA and contraction in the LV near the valve or basal region of the LV.

For the situation of a PVC, non-sustained ventricular tachyarrhythmia or post-shock, the control circuit 415 may change the set of active pacing channels to provide the best outcome in terms of contractility in light of the resulting conduction changes. In the example of FIG. 1, there are four LV pacing channels available and one or more RV pacing channels available. If less than all of the available pacing channels are being used in the first LV pacing mode, the control circuit 415 may activate a different set of pacing channels when operating in the second LV pacing mode than when operating in the first LV pacing mode.

In some examples the control circuit 415 may increase or decrease the number of active pacing channels between the first LV pacing mode and the second pacing mode. For instance, the control circuit may change between bi-ventricular RV and LV pacing, biventricular with RV and two or more LV pacing sites, LV pacing only with one LV site or multiple LV sites, or change to or from an RV only pacing mode, when switching back and forth between the pacing modes.

In some examples, the control circuit 415 activates the pacing channels in a first specified sequence when in the first multi-site LV pacing mode and in a second specified sequence when in the second LV pacing mode. The second sequence is different from the first sequence. For instance, in the example of FIG. 1, the first LV pacing mode may involve activating RV electrode 135 first, LV electrode 165 second, followed by LV electrodes 160, 164, 162. In the second LV pacing mode an LV electrode may activated before the RV electrode 135. Changing the active LV pacing channels may also include changing the amplitude or pulse width of the electrical pulses to change the electrical pulse energy. This may be necessary due to different thresholds required to capture the cardiac tissue at the different locations of the ventricles.

Changing the set of active pacing channels may have additional benefits for the patient beyond improving LV pacing therapy. It has been shown that myocardial regions experiencing low stress near LV pacing sites may improve myocardial gene and protein expression. Rotational pacing that entails deliberately moving the pacing site or sites around the available or candidate LV electrodes may spread that benefit around the LV myocardium.

Figure 5A:
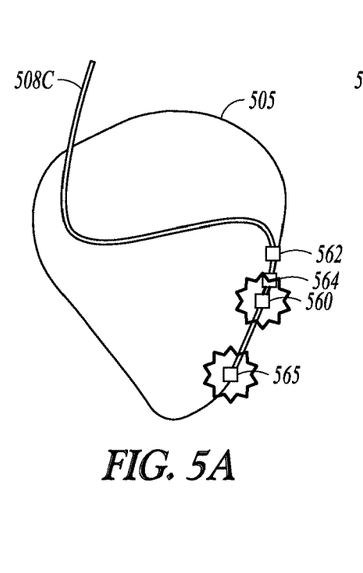
FIGS. 5A-5D are illustrations of an example of rotational pacing in the left ventricle.
Figure 5B:
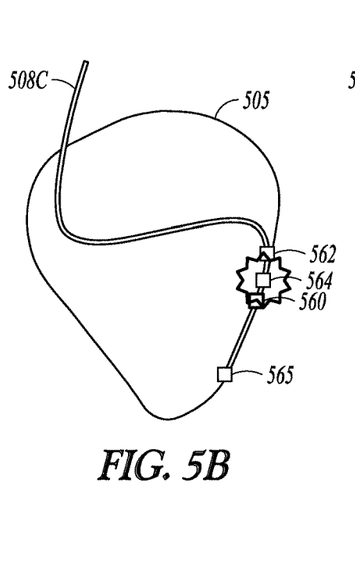
Figure 5C:
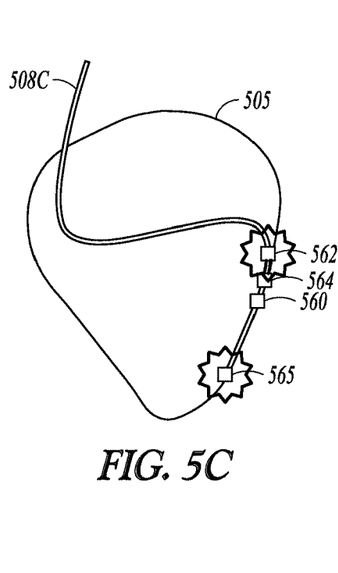
Figure 5D:
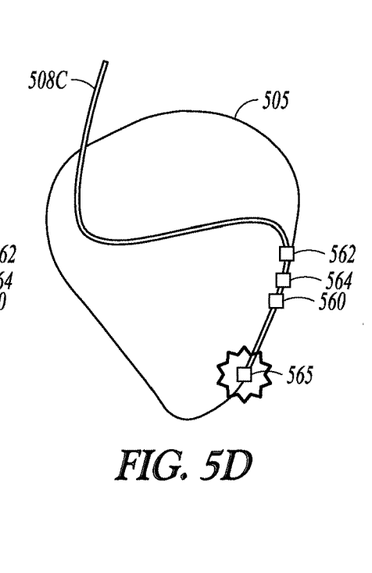

FIGS. 5A-5D are illustrations of an example of rotational pacing in the LV. Electrical pacing pulse energy is delivered to the heart 505 using electrodes included in an LV lead 508C. The pacing energy can be delivered in a single-site LV pacing mode and in a multi-site LV pacing mode. In FIG. 5A, electrical pulse energy is delivered using LV electrodes 565, 560, and 564. In FIG. 5B, electrical pulse energy is delivered using LV electrodes 560 and 564. In FIG. 5C, electrical pulse energy is delivered using LV electrodes 565, 564, and 562. In FIG. 5D electrical pulse energy is delivered using only LV electrode 565. The active LV pacing channel or channels can be changed when the control circuit changes operation between the first LV pacing mode and the second LV pacing mode. In some examples, the control circuit may recurrently select a different LV pacing channel or set of channels for one or both of the first LV pacing mode and the second LV pacing mode when that LV pacing mode is activated.

Returning to FIG. 4, in addition (or alternatively) to the change in the LV pacing site or sites, the control circuit 415 can change the inter-electrode stimulus timing used in the second LV pacing from the inter-electrode stimulus timing used in the first LV pacing mode. If an RV pacing channel is available, the inter-electrode stimulus timing can include LV-LV timing and LV-RV timing. The control circuit 415 can deliver electrical pulse energy to the LV and RV electrodes using a first LV-LV inter-electrode delay between the first LV electrode and the second LV electrode, and a second LV-RV inter-electrode delay between the second LV electrode and the RV electrode when operating in the first LV pacing mode. As explained in regard to FIG. 2, the control circuit 415 can change one or both of the LV-LV inter-electrode delay and the LV-RV inter-electrode delay when operating in the second LV pacing mode.

In some examples, the parameters can include the sensed atrial-ventricular delay (sensed AVD). The control circuit 415 may initiate delivery of electrical pulse energy to the LV following the intrinsic atrial event using a sensed AVD when operating in the first multi-site LV pacing mode, and initiate delivery of electrical pulse energy to the LV following an atrial paced event using a paced AV delay (paced AVD) when in the second LV pacing mode. The paced AVD may be set longer than the sensed AVD to allow more time for the slower conduction paths involved when pacing the atrium.

The inter-electrode stimulus timing can include multiple LV-LV inter-electrode times if there are three or more LV pacing channels available. In some examples, the inter-electrode times are shortened uniformly when changing operation from the first LV pacing mode to the second LV pacing mode. For instance all the inter-electrode delays in the second LV pacing mode (whether LV-LV or LV-RV) can be reduced or squeezed 70% from the inter-electrode delays on the first LV pacing mode. In some examples, different inter-electrode delays are shortened by a different amount instead of being shortened uniformly.

Figure 6:
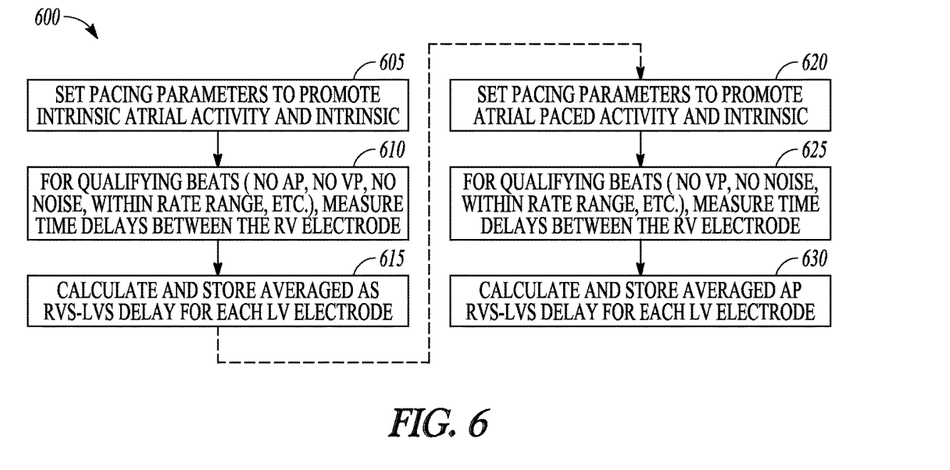
FIG. 6 is a flow diagram of another example of a method of controlling operation of an ambulatory medical device.

FIG. 6 is a flow diagram of an example of a method 600 of operating an ambulatory medical device to gather data to determine multi-site pacing parameters for the different LV pacing modes. The parameters can be determined by the device during a set-up operation performed within a specified timeframe from device activation or the set-up operation can be recurrently performed according to a schedule. The parameters can be determined during a session scheduled by a remote device (e.g., a remote server system), or during a session initiated by a clinician. The multi-site pacing parameters can be device determined but verified by the clinician (e.g., device performs measurements and presents parameter recommendations that are confirmed or finalized by a clinician).

In the example of FIG. 6, the parameters for a sensed event are determined first, but the parameters for the paced event may be determined first. The device may enter a test pacing mode to determine the parameters. At 605, the pacing parameters of the device are set (e.g., by the control circuit of the ambulatory medical device or by an external device) to promote intrinsic atrial activity and intrinsic ventricular activity. At 610, the time delays between the RV electrode and each LV electrode are measured for each qualifying heartbeat that occurs. Qualifying heartbeats include no atrial paced events, no ventricular paced events, and may additionally be required to have no noise interference, to be within the desired depolarization rate, etc. Other time delays such as the Q-wave to LV time delay may also be of interest. (A Q-wave refers to the deflection of a QRS complex that precedes the R-wave. The QRS complex of a surface electrocardiograph or an internal electrogram is associated with RV and LV depolarization.) At 615, the ambulatory medical device or the external device calculates and stores an average or other central tendency of the atrial sense RV-LV and LV-LV timing delays. Averaged AV delays can also be calculated and stored.

At 620, the pacing parameters of the device are set to promote atrial paced activity and intrinsic ventricular activity. At 625, the time delays between the RV electrode and each LV electrode measured for each qualifying heartbeat that occurs. Qualifying heart beats include no ventricular paced events, have no noise interference, and are within the desired depolarization rate. At 630, the central tendency of the atrial pace RV-LV and LV-LV timing delays and AV timing delays can be calculated and stored. In certain examples, phrenic nerve stimulation (PNS) thresholds and cardiac capture thresholds for electrodes can be determined to identify preferred electrodes for use in the first LV pacing mode and the second LV pacing mode. Other parameters can include amplitude or pulse width of the electrical pulse energy delivered. One or both of the amplitude and pulse width can be different between the first LV pacing mode and the second LV pacing mode.

The examples have been described referring to two different LV pacing modes. However, parameters for more than two LV pacing modes may be stored and the parameters can be loaded based on the type of cardiac event detected or determined. For instance, the four examples of LV pacing shown in FIGS. 5A-5D may be four LV pacing modes selected according to the cardiac event. One LV pacing mode is selected when the cardiac event is a change from atrial sense to atrial pace, a second LV pacing mode may be selected when one or more PVCs are detected, a third LV pacing mode may be selected when a non-sustained ventricular tachyarrhythmia is detected, a fourth LV pacing mode may be selected when the patient is in a post-shock condition, and a fifth pacing mode may be selected for periods of deliberate rotational pacing amongst the LV electrodes. In some examples, the fifth pacing mode may be recurrently selected in the absence of the triggers for the other four pacing modes. The several pacing modes may include different inter-electrode timing and different pacing energy as well as the different pacing sites.

Figure 7:
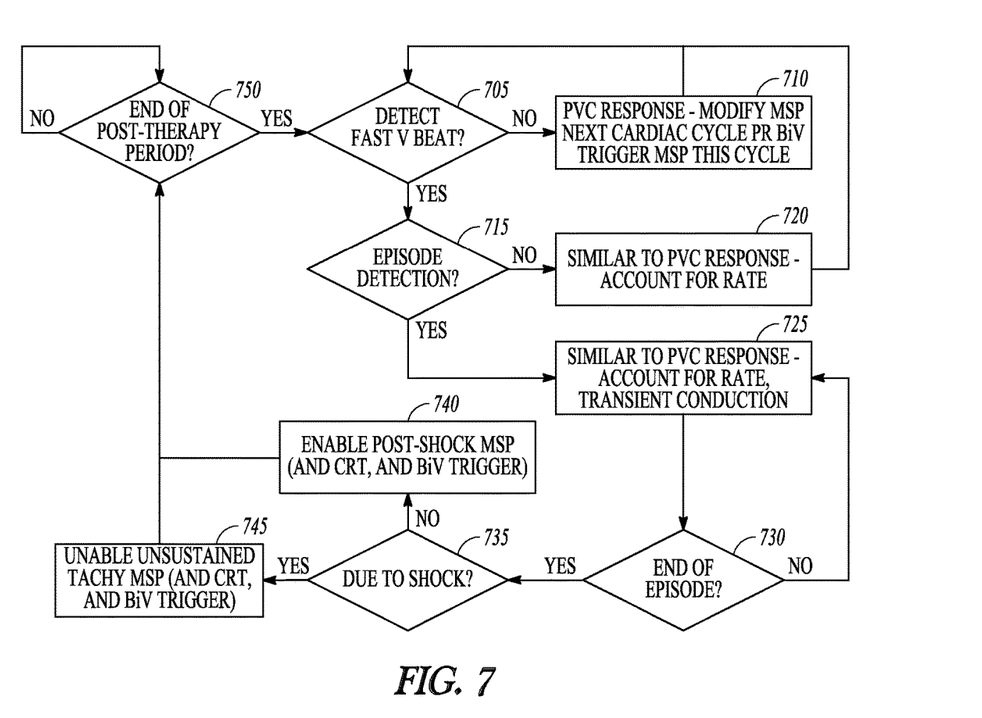
FIG. 7 is a flow diagram of an example of changing multi-site pacing modes of an ambulatory medical device.

FIG. 7 is a flow diagram of an example of changing multi-site LV pacing modes of an ambulatory medical device determined according to the type of cardiac event occurring for the patient. At 705 the device determines if one or more fast ventricular beats were detected. Heartbeats may be identified as fast beats when the beats satisfy a specified VF detection interval threshold, or the interval of the fast beats is less than or equal to a specified interval threshold (e.g., 260 ms). If fast beats are not detected, the cardiac event may be a PVC and the parameters for the PVC response are loaded by the device at 710. The parameters may be loaded at the next cardiac cycle or loading of the parameters may be triggered for the present cardiac cycle (e.g., when the device is providing bi-ventricular (BiV) pacing therapy). Loading the parameters for the LV pacing mode to respond to the PVC response may adjust one or more of the pacing sites used, the inter-electrode timing, and the pacing energy delivered. Changing the LV pacing mode to respond to PVCs may prevent the start of ventricular tachyarrhythmia by changing the conduction paths.

Returning to 705, if fast beats are detected it is determined at 715 if the patient is experiencing an episode of ventricular tachyarrhythmia. This can be determined using a second tier of ventricular tachyarrhythmia detection after the initial fast heart beat detection (e.g., using an assessment of heart rate stability). If ventricular tachyarrhythmia is not indicated, the device loads parameters similar to those for the response to the PVC event at 720. The parameters for this LV pacing mode 720 may take into account a difference heart rate from the PVC response by reducing one or more inter-electrode time delays.

If ventricular tachyarrhythmia is indicated at 715, flow continues to 725 where the device loads parameters similar to those for response to the PVC event. The parameters for this LV pacing mode may take into account a difference heart rate from the PVC response by reducing one or more inter-electrode time delays and may take into account the transient conduction path by changing ventricular pacing sites. If the end of the episode of ventricular tachyarrhythmia is detected at 730 it is determined at 735 if the episode was terminated with high energy defibrillation/cardioversion shock therapy at 735.

If the episode was not terminated using shock therapy, the episode was non-sustained ventricular tachyarrhythmia and parameters for non-sustained ventricular tachyarrhythmia are loaded at 740. The parameters for this LV pacing mode may adjust one or both of the pacing sites and inter-electrode delays to account for transient conduction changes as the heart adjusts to the impact of unstable hemodynamics associated with the episode. This LV pacing mode can include triggering bi-ventricular pacing and CRT. The electrical pacing energy may also be adjusted if necessary to accommodate the new pacing channels used.

If the ventricular tachyarrhythmia episode was terminated with shock therapy, parameters for the post-shock LV pacing mode are loaded by the device at 745. The post-shock LV pacing mode can include triggering bi-ventricular pacing and CRT. The parameters for this LV pacing mode may include adjusting one or both of the pacing sites and the inter-electrode delays to account for conduction changes due to the shock or shocks delivered. The number of ventricular pacing sites may be increased and electrical pacing energy may be increased. PNS thresholds may be given a lower priority and allowed to be exceeded in this LV pacing mode. At 750 flow returns to the detection at 705 at the end of the post-therapy period. Not all of the decision branches need to be included in the example flow diagram of FIG. 7. For instance, the flow diagram may only include determinations for post-shock and non-sustained tachyarrhythmia, and only enable MSP for those conditions.

Figure 8:
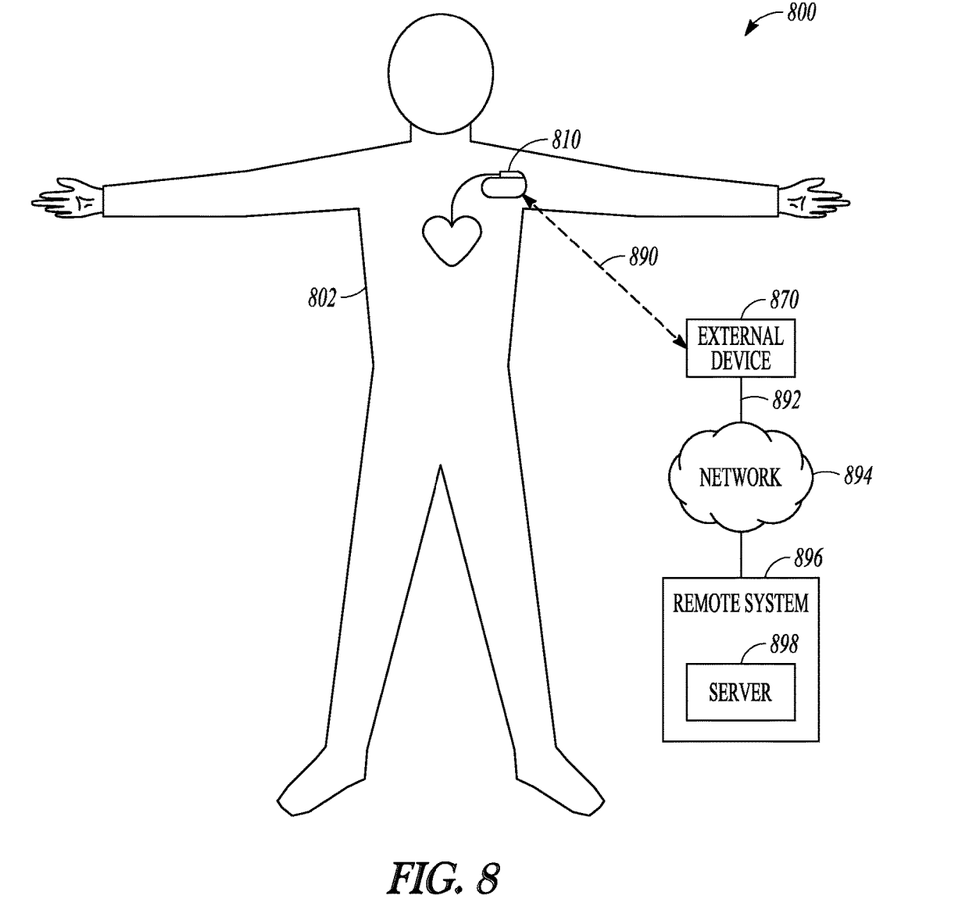
FIG. 8 is an illustration of portions of an example of a system that uses a deployed implantable medical device to provide a therapy to a patient.

FIG. 8 is an illustration of portions of a system 800 that uses an IMD 810 to provide a therapy to a patient 802. The system 800 typically includes an external device 870 that communicates signals 890 wirelessly with a remote system 896 via a network 894. The network 894 can be a communication network such as a phone network or a computer network (e.g., the internet). In some examples, the external device 870 includes a repeater and communicated via the network using a link 892 that may be wired or wireless. In some examples, the remote system 896 provides patient management functions and may include one or more servers 898 to perform the functions.

Returning to FIG. 4, the device 400 can include a communication circuit 435 to communicate information with a separate device, such as the external device 870 of FIG. 8. The external device can be used to program conditions for a set-up operation to determine parameters for multi-site LV pacing modes. Statistics on mode changing by the IMD 810 may be uploaded to the external device 870 for later inspection.

The optimum setting for the various multi-site LV pacing modes may vary over time for a patient due to maturation of myocardial tissue around an implanted electrode, drug therapy prescribed to the patient, an episode of myocardial infarction, and defibrillation of the myocardial tissue. Therefore, the set up operations may be run more than once by a device while the device is implanted.

The devices and methods described herein allow for multi-site stimulation to be adjusted to deliver the most effective therapy for the patient. The device may provide additional information related to the multi-site pacing to assist the clinician or caregiver in managing the device-based therapy.

ADDITIONAL DESCRIPTION AND EXAMPLES

Example 1 can include subject matter (such as an apparatus) comprising a cardiac signal sensing circuit configured to sense a cardiac activity signal using a sensing channel that includes implantable electrodes of the plurality of electrodes; a stimulus circuit configured to provide electrical pulse energy using at least a first left ventricular (LV) pacing channel that includes a first LV electrode and a second LV pacing channel that includes a second LV electrode; and a control circuit operatively coupled to the stimulus circuit and the cardiac signal sensing circuit and configured to: initiate delivery of electrical pulse energy using the first and second pacing channels according to a first multi-site LV pacing mode; determine a cardiac event associated with a change in cardiac conduction path using a sensed cardiac activity signal; and change to a second LV pacing mode in response to determining the cardiac event, wherein the second LV pacing mode is different from the first multi-site LV pacing mode in one or more of a pacing site location and an inter-electrode stimulus timing.

In Example 2, the subject matter of Example 1 optionally includes a stimulus circuit configured to provide electrical pulse energy using an atrial pacing channel that includes an atrial electrode, wherein the sensing channel includes the same or different atrial electrode, wherein the control circuit is configured to initiate delivery of electrical pulse energy according to the first multi-site LV pacing mode when sensing an intrinsic atrial event, and initiate delivery of electrical pulse energy according to the second LV pacing mode when determining that electrical pulse energy is to be delivered to an atrium.

In Example 3, the subject matter of Example 2 optionally includes a control circuit configured to initiate delivery of electrical pulse energy to the LV following the intrinsic atrial event using a sensed atrial-ventricular delay (AVD) when operating in the first multi-site LV pacing mode, and initiate delivery of electrical pulse energy to the LV following delivery of electrical pulse energy to the atrium using a paced AVD when in the second LV pacing mode, wherein the paced AVD is longer than the sensed AVD.

In Example 4, the subject matter of on or any combination of Examples 1-3 optionally includes a control circuit configured to initiate delivery of electrical pulse energy to a reduced number of pacing sites when operating in the second LV pacing mode than when operating in the first multi-site LV pacing mode.

In Example 5, the subject matter of one or any combination of Examples 1-4 optionally includes a control circuit configured to initiate a test pacing mode to determine one or more parameters for the first multi-site LV pacing mode and determine one or more parameters for the second LV pacing mode.

In Example 6, the subject matter of one or any combination of Examples 1-5 optionally includes an implantable lead that includes at least the first LV electrode and the second LV electrode, wherein the control circuit is configured to exclude delivery of electrical pulse energy to a most proximal LV electrode of the implantable lead when operating in the second LV pacing mode.

In Example 7, the subject matter of one or any combination of Examples 1-6 optionally includes a stimulus circuit is configured to provide electrical pulse energy using a right ventricular (RV) pacing channel that includes an RV electrode, wherein the control circuit is configured to: deliver electrical pulse energy to the LV and RV electrodes using a first inter-electrode delay between the first LV electrode and the second LV electrode, and a second inter-electrode delay between the second LV electrode and the RV electrode when operating in the first multi-site LV pacing mode; and change one or both of the first inter-electrode delay and the second inter-electrode delay when operating in the second LV pacing mode.

In Example 8, the subject matter of one or any combination of Examples 1-7 optionally includes a stimulus circuit configured to provide electrical pulse energy to a plurality of pacing channels that include the plurality of implantable electrodes, wherein the control circuit is configured to: activate a first set of candidate pacing channels from the plurality of pacing channels when delivering electrical pulse energy according to the first multi-site LV pacing mode, and activate a second set of candidate pacing channels different from the first set of candidate pacing channels when delivering electrical pulse energy according to the second LV pacing mode.

In Example 9, the subject matter of one or any combination of Examples 1-8 optionally includes a control circuit configured to recurrently select a different pacing channel from activated candidate pacing channels for delivery of electrical pulse energy.

In Example 10, the subject matter of one or any combination of Examples 1-9 optionally includes a control circuit configured to detect a premature ventricular contraction (PVC) and initiate delivery of electrical pulse energy according to the second LV pacing mode when detecting the PVC.

In Example 11, the subject matter of one or any combination of Examples 1-10 optionally includes a control circuit configured to detect an episode of non-sustained ventricular tachyarrhythmia and initiate delivery of electrical pulse energy according to the second LV pacing mode when detecting the episode of non-sustained ventricular tachyarrhythmia, In Example 12, the subject matter of one or any combination of Example 1-11 optionally includes a control circuit configured to determine when high energy electrical shock therapy is delivered to the patient and initiate delivery of lower energy electrical pulse energy according to the second LV pacing mode after delivery of the high energy electrical shock therapy.

In Example 13, the subject matter of one or any combination of Examples 1-12 optionally includes a stimulus circuit configured to provide electrical pulse energy using a right ventricular (RV) pacing channel that includes an RV electrode and at least a third LV pacing channel that includes a third LV electrode, wherein the control circuit is configured to activate a different set of available pacing channels when operating in the second LV pacing mode than when operating in the first multi-site LV pacing mode.

In Example 14, the subject matter of one or any combination of Examples 1-13 optionally includes a stimulus circuit configured to provide electrical pulse energy using a right ventricular (RV) pacing channel that includes an RV electrode, wherein the control circuit is configured to initiate delivery of electrical pulse energy to the pacing channels in a first specified sequence when in the first multi-site LV pacing mode and in a second specified sequence when in the second LV pacing mode, wherein the second specified sequence is different from the first specified sequence.

Example 15 can include subject matter (such as a method of operating an ambulatory medical device, a means for performing acts, or a machine-readable medium including instructions that, when performed by the machine, cause the machine to perform acts), or can optionally be combined with the subject matter of one or any combination of Examples 1-14 to include such subject matter, comprising: sensing a cardiac activity signal using a sensing channel that includes an electrode implantable in at least one of an atrium or ventricle of a subject; delivering electrical pulse energy according to a first multi-site left ventricular (LV) pacing mode using at least a first LV pacing channel that includes a first LV electrode and a second LV pacing channel that includes a second LV electrode; determining a cardiac event associated with a change in cardiac conduction path using the sensed cardiac activity signal; and changing to a second LV pacing mode in response to determining the cardiac event, wherein the second LV pacing mode is different from the first multi-site LV pacing mode in one or more of a pacing site location and an inter-electrode stimulus timing.

In Example 16, the subject matter of Example 15 optionally includes: sensing a cardiac activity signal using the sensing channel, wherein the sensing channel includes an electrode implantable in the atrium; delivering electrical pulse energy to the LV according to the first multi-site LV pacing mode when sensing an intrinsic atrial event; and delivering electrical pulse energy to the LV according to the second LV pacing mode in absence of the intrinsic atrial event and delivery of electrical pulse energy to the atrium is scheduled by the implantable medical device.

In Example 17 the subject matter of Example 15 or 16 optionally includes delivering electrical pulse energy to the LV according to the second LV pacing mode when detecting at least one of a premature ventricular contraction (PVC), a non-sustained episode of ventricular tachyarrhythmia, or that high energy electrical shock therapy was delivered to the subject.

Example 18 can include subject matter (such as a system) or can optionally be combined with the subject matter of one or any combination of Examples 1-17 to include such subject matter, comprising: a first implantable lead including a plurality of electrodes implantable in a left ventricle (LV) of a subject; a second implantable lead including at least one electrode implantable in a right ventricle (RV) of the subject; and an implantable medical device electrically coupled to the implantable leads, wherein the implantable medical device includes: a housing including an implantable electrode incorporated into the housing; a cardiac signal sensing circuit configured to sense a cardiac activity signal using a sensing channel that includes at least two of the implantable electrodes; a stimulus circuit configured to provide electrical pulse energy using at least a first left ventricular (LV) pacing channel that includes a first LV electrode, a second LV pacing channel that includes a second LV electrode, and a third LV pacing channel that includes a third LV electrode; and a control circuit operatively coupled to the stimulus circuit and the cardiac signal sensing circuit and configured to: initiate delivery of electrical pulse energy to the first and second pacing channels according to a first multi-site LV pacing mode; determine a cardiac event associated with a change in cardiac conduction path using a sensed cardiac activity signal; and change to a second multi-site LV pacing mode in response to determining the cardiac event, wherein the second multi-site LV pacing mode is different from the first multi-site LV pacing mode in one or more of a pacing site location and an inter-electrode stimulus timing.

In Example 19, the subject matter of Example 18 optionally includes a control circuit configured to detect at least one of a premature ventricular contraction (PVC) or a non-sustained episode of ventricular tachyarrhythmia, and operate in the second multi-site LV pacing mode when detecting the at least one of the PVC or the non-sustained episode of ventricular tachyarrhythmia, wherein the control circuit is configured to activate a different set of available pacing channels when operating in the second multi-site LV pacing mode than when operating in the first multi-site LV pacing mode.

In Example 20, the subject matter of one or both of Examples 18 and 19 optionally includes a control circuit configured to initiate delivery of electrical pulse energy to the pacing channels in a first specified sequence when in the first multi-site LV pacing mode and in a second specified sequence when in the second multi-site LV pacing mode, wherein the second specified sequence is different from the first specified sequence.

Example 21 can include, or can optionally be combined with any portion or combination of any portions of any one or more of Examples 1-20 to include, subject matter that can include means for performing any one or more of the functions of Examples 1-20, or a machine-readable medium including instructions that, when performed by a machine, cause the machine to perform any one or more of the functions of Examples 1-20.

These non-limiting examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like. In some examples, a carrier medium can carry code implementing the methods. The term "carrier medium" can be used to represent carrier waves on which code is transmitted.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus for electrical coupling to a plurality of implantable electrodes, the apparatus comprising:
a cardiac signal sensing circuit configured to sense a cardiac activity signal using a sensing channel that includes implantable electrodes of the plurality of electrodes;
a stimulus circuit configured to provide electrical pulse energy using at least a first left ventricular (LV) pacing channel that includes a first LV electrode and a second LV pacing channel that includes a second LV electrode; and
a control circuit operatively coupled to the stimulus circuit and the cardiac signal sensing circuit and configured to:
initiate delivery of electrical pulse energy using the first and second pacing channels according to a first multi-site LV pacing mode;
determine a cardiac event associated with a change in cardiac conduction path using a sensed cardiac activity signal; and
change to a second LV pacing mode in response to determining the cardiac event, wherein the second LV pacing mode is different from the first multi-site LV pacing mode in one or more of a pacing site location and inter-electrode stimulus timing.

2. The apparatus of claim 1, wherein the stimulus circuit is configured to provide electrical pulse energy using an atrial pacing channel that includes an atrial electrode, wherein the sensing channel includes the same or different atrial electrode, wherein the control circuit is configured to initiate delivery of electrical pulse energy according to the first multi-site LV pacing mode when sensing an intrinsic atrial event, and initiate delivery of electrical pulse energy according to the second LV pacing mode when determining that electrical pulse energy is to be delivered to an atrium.

3. The apparatus of claim 2, wherein the control circuit is configured to initiate delivery of electrical pulse energy to the LV following the intrinsic atrial event using a sensed atrial-ventricular delay (AVD) when operating in the first multi-site LV pacing mode, and initiate delivery of electrical pulse energy to the LV following delivery of electrical pulse energy to the atrium using a paced AVD when in the second LV pacing mode, wherein the paced AVD is longer than the sensed AVD.

4. The apparatus of claim 1, wherein the control circuit is configured to initiate delivery of electrical pulse energy to a reduced number of pacing sites when operating in the second LV pacing mode than when operating in the first multi-site LV pacing mode.

5. The apparatus of claim 1, wherein the control circuit is configured to initiate a test pacing mode to determine one or more parameters for the first multi-site LV pacing mode and determine one or more parameters for the second LV pacing mode.

6. The apparatus of claim 1, including an implantable lead that includes at least the first LV electrode and the second LV electrode, wherein the control circuit is configured to exclude delivery of electrical pulse energy to a most proximal LV electrode of the implantable lead when operating in the second LV pacing mode.

7. The apparatus of claim 1, wherein the stimulus circuit is configured to provide electrical pulse energy using a right ventricular (RV) pacing channel that includes an RV electrode, wherein the control circuit is configured to:
deliver electrical pulse energy to the LV and RV electrodes using a first inter-electrode delay between the first LV electrode and the second LV electrode, and a second inter-electrode delay between the second LV electrode and the RV electrode when operating in the first multi-site LV pacing mode; and
change one or both of the first inter-electrode delay and the second inter-electrode delay when operating in the second LV pacing mode.

8. The apparatus of claim 1,
wherein the stimulus circuit is configured to provide electrical pulse energy to a plurality of pacing channels that include the plurality of implantable electrodes,
wherein the control circuit is configured to: activate a first set of candidate pacing channels from the plurality of pacing channels when delivering electrical pulse energy according to the first multi-site LV pacing mode, and activate a second set of candidate pacing channels different from the first set of candidate pacing channels when delivering electrical pulse energy according to the second LV pacing mode.

9. The apparatus of claim 8, wherein the control circuit is configured to recurrently select a different pacing channel from activated candidate pacing channels for delivery of electrical pulse energy.

10. The apparatus of claim 1, wherein the control circuit is configured to detect a premature ventricular contraction (PVC) and initiate delivery of electrical pulse energy according to the second LV pacing mode when detecting the PVC.

11. The apparatus of claim 1, wherein the control circuit is configured to detect an episode of non-sustained ventricular tachyarrhythmia and initiate delivery of electrical pulse energy according to the second LV pacing mode when detecting the episode of non-sustained ventricular tachyarrhythmia.

12. The apparatus of claim 1, wherein the control circuit is configured to determine when high energy electrical shock therapy is delivered to the patient and initiate delivery of lower energy electrical pulse energy according to the second LV pacing mode after delivery of the high energy electrical shock therapy.

13. The apparatus of claim 1, wherein the stimulus circuit is configured to provide electrical pulse energy using a right ventricular (RV) pacing channel that includes an RV electrode and at least a third LV pacing channel that includes a third LV electrode, wherein the control circuit is configured to activate a different set of available pacing channels when operating in the second LV pacing mode than when operating in the first multi-site LV pacing mode.

14. The apparatus of claim 1, wherein the stimulus circuit is configured to provide electrical pulse energy using a right ventricular (RV) pacing channel that includes an RV electrode, wherein the control circuit is configured to initiate delivery of electrical pulse energy to the pacing channels in a first specified sequence when in the first multi-site LV pacing mode and in a second specified sequence when in the second LV pacing mode, wherein the second specified sequence is different from the first specified sequence.

15. A method of controlling operation of an implantable medical device (IMD), the method comprising:
sensing a cardiac activity signal using a sensing channel that includes an electrode implantable in at least one of an atrium or ventricle of a subject;
delivering electrical pulse energy according to a first multi-site left ventricular (LV) pacing mode using at least a first LV pacing channel that includes a first LV electrode and a second LV pacing channel that includes a second LV electrode;
determining a cardiac event associated with a change in cardiac conduction path using the sensed cardiac activity signal; and
changing to a second LV pacing mode in response to determining the cardiac event, wherein the second LV pacing mode is different from the first multi-site LV pacing mode in one or more of a pacing site location and an inter-electrode stimulus timing.

16. The method of claim 15, including:
sensing a cardiac activity signal using the sensing channel, wherein the sensing channel includes an electrode implantable in the atrium;
delivering electrical pulse energy to the LV according to the first multi-site LV pacing mode when sensing an intrinsic atrial event; and
delivering electrical pulse energy to the LV according to the second LV pacing mode in absence of the intrinsic atrial event and delivery of electrical pulse energy to the atrium is scheduled by the implantable medical device.

17. The method of claim 15, including delivering electrical pulse energy to the LV according to the second LV pacing mode when detecting at least one of a premature ventricular contraction (PVC), a non-sustained episode of ventricular tachyarrhythmia, or that high energy electrical shock therapy was delivered to the subject.

18. A system comprising:
a first implantable lead including a plurality of electrodes implantable in a left ventricle (LV) of a subject;
a second implantable lead including at least one electrode implantable in a right ventricle (RV) of the subject; and
an implantable medical device electrically coupled to the implantable leads, wherein the implantable medical device includes:
a housing including an implantable electrode incorporated into the housing;
a cardiac signal sensing circuit configured to sense a cardiac activity signal using a sensing channel that includes at least two of the implantable electrodes;
a stimulus circuit configured to provide electrical pulse energy using at least a first left ventricular (LV) pacing channel that includes a first LV electrode, a second LV pacing channel that includes a second LV electrode, and a third LV pacing channel that includes a third LV electrode; and
a control circuit operatively coupled to the stimulus circuit and the cardiac signal sensing circuit and configured to:
initiate delivery of electrical pulse energy to the first and second pacing channels according to a first multi-site LV pacing mode;
determine a cardiac event associated with a change in cardiac conduction path using a sensed cardiac activity signal; and
change to a second multi-site LV pacing mode in response to determining the cardiac event, wherein the second multi-site LV pacing mode is different from the first multi-site LV pacing mode in one or more of a pacing site location and an inter-electrode stimulus timing.

19. The system of claim 18, wherein the control circuit is configured to detect at least one of a premature ventricular contraction (PVC) or a non-sustained episode of ventricular tachyarrhythmia, and operate in the second multi-site LV pacing mode when detecting the at least one of the PVC or the non-sustained episode of ventricular tachyarrhythmia, wherein the control circuit is configured to activate a different set of available pacing channels when operating in the second multi-site LV pacing mode than when operating in the first multi-site LV pacing mode.

20. The system of claim 18, wherein the control circuit is configured to initiate delivery of electrical pulse energy to the pacing channels in a first specified sequence when in the first multi-site LV pacing mode and in a second specified sequence when in the second multi-site LV pacing mode, wherein the second specified sequence is different from the first specified sequence.

* * * * *